United States Patent
Fujikawa

(10) Patent No.: US 11,771,603 B2
(45) Date of Patent: Oct. 3, 2023

(54) ABSORBENT ARTICLE

(71) Applicant: The Procter & Gamble Company, Cincinnati, OH (US)

(72) Inventor: Hiroshi Fujikawa, Himeji (JP)

(73) Assignee: The Procter & Gamble Company, Cincinnati, OH (US)

( * ) Notice: Subject to any disclaimer, the term of this patent is extended or adjusted under 35 U.S.C. 154(b) by 554 days.

(21) Appl. No.: 17/005,377

(22) Filed: Aug. 28, 2020

(65) Prior Publication Data

US 2021/0059873 A1    Mar. 4, 2021

Related U.S. Application Data

(60) Provisional application No. 62/894,861, filed on Sep. 2, 2019.

(51) Int. Cl.
*A61F 13/15* (2006.01)
*A61F 13/511* (2006.01)
(Continued)

(52) U.S. Cl.
CPC ........ *A61F 13/51121* (2013.01); *A61F 13/47* (2013.01); *A61F 13/496* (2013.01); *A61F 13/51113* (2013.01); *A61F 13/53* (2013.01); *A61L 15/20* (2013.01); *A61L 15/48* (2013.01); *A61F 2013/1591* (2013.01); *A61F 2013/15967* (2013.01); *A61F 2013/51059* (2013.01); *A61F 2013/51178* (2013.01); *A61F 2013/530306* (2013.01); *A61F 2013/53908* (2013.01)

(58) Field of Classification Search
CPC .. A61F 13/51121; A61F 13/47; A61F 13/496; A61F 13/5113; A61F 13/53; A61F 2013/1591; A61F 2013/15967; A61F 2013/51059; A61F 2013/51178; A61F 2013/5303; A61F 2013/53908; A61L 15/20; A61L 15/48
See application file for complete search history.

(56) References Cited

U.S. PATENT DOCUMENTS 3,848,594 A    11/1974   Buell
3,860,003 A     1/1975   Buell
(Continued)

FOREIGN PATENT DOCUMENTS

CN       1599585 A    3/2005
CN     202714984 U    2/2013
(Continued)

OTHER PUBLICATIONS

International Search Report and Written Opinion; Application Ser. No. PCT/US2020/048856, dated Dec. 15, 2020, 8 pages.

*Primary Examiner* — Jacqueline F Stephens
(74) *Attorney, Agent, or Firm* — Charles R. Matson

(57) ABSTRACT

Disclosed is an absorbent article comprising; (a) a topsheet having a skin facing side and a core facing side, the topsheet being liquid permeable and having the core facing side coated with at least about 0.01 mg/m², preferably from about 0.05 mg/m² to about 0.2 mg/m², of calcium carbonate; (b) a backsheet which is liquid impermeable; and (c) an absorbent core comprising an absorbent material, the absorbent core disposed between the topsheet and the backsheet.

12 Claims, 4 Drawing Sheets

(51) Int. Cl.
  *A61F 13/47* (2006.01)
  *A61F 13/496* (2006.01)
  *A61F 13/53* (2006.01)
  *A61L 15/20* (2006.01)
  *A61L 15/48* (2006.01)
  *A61F 13/51* (2006.01)
  *A61F 13/539* (2006.01)

(56) References Cited

U.S. PATENT DOCUMENTS

| | | | |
|---|---|---|---|
| 3,929,135 A | 12/1975 | Thompson | |
| 4,324,246 A * | 4/1982 | Mullane | A61F 13/51305 604/371 |
| 4,342,314 A | 8/1982 | Radel et al. | |
| 4,463,045 A | 7/1984 | Ahr et al. | |
| 4,515,595 A | 5/1985 | Kievit et al. | |
| 4,609,518 A | 9/1986 | Curro et al. | |
| 4,629,643 A | 12/1986 | Curro et al. | |
| 4,662,875 A | 5/1987 | Hirotsu et al. | |
| 4,681,793 A | 7/1987 | Linman et al. | |
| 4,695,278 A | 9/1987 | Lawson | |
| 4,710,189 A | 12/1987 | Lash | |
| 4,795,454 A * | 1/1989 | Dragoo | A61F 13/4942 604/385.27 |
| 4,808,178 A | 2/1989 | Aziz et al. | |
| 4,846,815 A | 7/1989 | Schipps | |
| 4,894,060 A | 1/1990 | Nestgard | |
| 4,917,697 A | 4/1990 | Osborn, III et al. | |
| 4,946,527 A | 8/1990 | Battrell | |
| 4,963,140 A | 10/1990 | Robertson et al. | |
| 5,006,394 A | 4/1991 | Baird | |
| 5,137,537 A | 8/1992 | Herron et al. | |
| 5,151,092 A | 9/1992 | Buell et al. | |
| 5,221,274 A | 6/1993 | Buell et al. | |
| 5,549,791 A | 8/1996 | Herron et al. | |
| 5,554,145 A | 9/1996 | Roe et al. | |
| 5,569,234 A | 10/1996 | Buell et al. | |
| 5,571,096 A | 11/1996 | Dorbin et al. | |
| 5,580,411 A | 12/1996 | Nease et al. | |
| 5,607,760 A | 3/1997 | Roe | |
| 5,609,587 A * | 3/1997 | Roe | A61L 15/34 604/360 |
| 5,643,588 A | 7/1997 | Roe et al. | |
| 5,700,254 A | 12/1997 | McDowall et al. | |
| 5,865,823 A | 2/1999 | Curro | |
| 5,938,648 A | 8/1999 | LaVon et al. | |
| 5,968,025 A | 10/1999 | Roe et al. | |
| 6,004,306 A | 12/1999 | Robles et al. | |
| 6,432,098 B1 | 8/2002 | Kline et al. | |
| 6,645,569 B2 | 11/2003 | Cramer et al. | |
| 6,716,441 B1 | 4/2004 | Osborne et al. | |
| 6,863,933 B2 | 3/2005 | Cramer et al. | |
| 6,946,585 B2 | 9/2005 | London Brown | |
| 7,112,621 B2 | 9/2006 | Rohrbaugh et al. | |
| 7,786,341 B2 | 8/2010 | Schneider et al. | |
| 2003/0148684 A1 | 8/2003 | Cramer et al. | |
| 2005/0008839 A1 | 1/2005 | Cramer et al. | |
| 2005/0256476 A1 * | 11/2005 | Mirle | A61F 13/514 604/382 |
| 2007/0118087 A1 | 5/2007 | Flohr et al. | |
| 2008/0312622 A1 | 12/2008 | Hundorf et al. | |
| 2011/0250413 A1 | 10/2011 | Lu et al. | |
| 2011/0268932 A1 | 11/2011 | Catalan et al. | |
| 2011/0319848 A1 | 12/2011 | McKiernan et al. | |
| 2017/0079858 A1 | 3/2017 | Willhaus et al. | |
| 2019/0000688 A1 | 1/2019 | Bianchi et al. | |

FOREIGN PATENT DOCUMENTS

| | | | |
|---|---|---|---|
| EP | 1417945 A1 | 5/2004 | |
| EP | 2957301 A1 * | 12/2015 | A61L 2/00 |
| EP | 3378502 A1 * | 9/2018 | A61F 13/51113 |
| JP | H10219568 | 8/1998 | |
| JP | 2001137285 | 5/2001 | |
| WO | WO 9510996 | 4/1995 | |
| WO | WO 9516746 | 6/1995 | |
| WO | WO 9524173 | 9/1995 | |
| WO | WO 9534329 | 12/1995 | |
| WO | WO 0059430 | 10/2000 | |
| WO | WO 02064877 | 8/2002 | |
| WO | WO 02067809 | 9/2002 | |
| WO | WO 2011087503 | 7/2011 | |
| WO | WO 2015134359 | 9/2015 | |

\* cited by examiner

ABSORBENT ARTICLE

CROSS REFERENCE TO RELATED APPLICATION

This application claims the benefit of U.S. Provisional Application No. 62/894,861, filed on Sep. 2, 2019, which is incorporated by reference herein.

FIELD OF THE INVENTION

The present invention relates to an absorbent article having improved fluid handling properties.

BACKGROUND OF THE INVENTION

Absorbent articles for personal hygiene, such as disposable diapers, disposable pants, adult incontinence undergarments, and sanitary napkins, are designed to absorb and contain body exudates, in particular urine, low viscosity fecal matter, and menses (collectively described herein as "fluids"). These absorbent articles may comprise several layers providing different functions, for example, a topsheet, a backsheet, and an absorbent core disposed between the topsheet and the backsheet, among other layers, if desired.

The topsheet is generally liquid permeable and is configured to receive the fluids and aid in directing the fluid towards the absorbent core. In general, topsheets are nonwoven fabrics made of hydrophobic fibers, and made to have higher hydrophilicity via a hydrophilic surfactant treatment applied to the skin-facing surface thereto so that the fluids are attracted to the topsheet and then be channeled into the underlying layers. One of the important qualities of a topsheet is the ability to reduce residency time of the fluids on the topsheet before the fluids are able to be absorbed by the absorbent core. Thus, one criteria of topsheet quality is to reduce the amount of time the fluids spend on the topsheets prior to being absorbed by the absorbent core. If the fluids remain on the surface of the topsheet for too long of a period of time, this may lead to various performance disadvantages. For example, the fluid remaining on the surface of the topsheet may move according to the movement of the wearer and cause leakage. The remaining fluid may cause wet feeling, discomfort, and even skin rash problems to the wearer.

Meanwhile, nonwoven fabrics for forming the topsheet are typically supplied to the manufacturer with surfactant treatment already provided. During processing of the topsheet material for assembling the absorbent article, at least some of the surfactant provided on the topsheet may be removed due to friction with machinery surfaces. Such removal of surfactant is a negative factor for reducing residency time of the fluids on the topsheet. Further, for addressing the skin health concern of the wearer, it is common practice to further coat the skin facing surface of the topsheet with a lotion. Such lotion composition typically comprises hydrophobic components which may adversely affect the fluid absorption speed of the topsheet. As such, while use of lotion on the topsheet is desired for promoting skin health, ironically this may also increase the residency time of fluid on the topsheet.

To address the problem of prolonged fluid residency on topsheets, what has been proposed is, for example, providing apertures to allow for faster fluid penetration, and/or providing three-dimensional deformations to reduce contact with the skin, such as those disclosed in PCT publication WO 2015/134359 A. It has been found, however, that despite the upcharge such processed topsheets may require, the benefit in increasing fluid penetration may not be as significant. Further, in view of the recent desire of the consumer to use products which are environmentally friendly, there is greater pressure to use as little material as possible for absorbent articles. In order to meet such consumer needs, topsheets made of less material and still having good fluid handling properties are desired.

Based on the foregoing, there is a need for an absorbent article having a topsheet with improved fluid handling properties. There is also a need for an absorbent article which may be economically manufactured.

SUMMARY OF THE INVENTION

The present invention is directed to an absorbent article comprising;
(a) a topsheet having a skin facing side and a core facing side, the topsheet being liquid permeable and having the core facing side coated with at least about 0.01 mg/m$^2$, preferably from about 0.05 mg/m$^2$ to about 0.2 mg/m$^2$, of calcium carbonate;
(b) a backsheet which is liquid impermeable; and
(c) an absorbent core comprising an absorbent material, the absorbent core disposed between the topsheet and the backsheet.

DEFINITIONS

Figure 1:
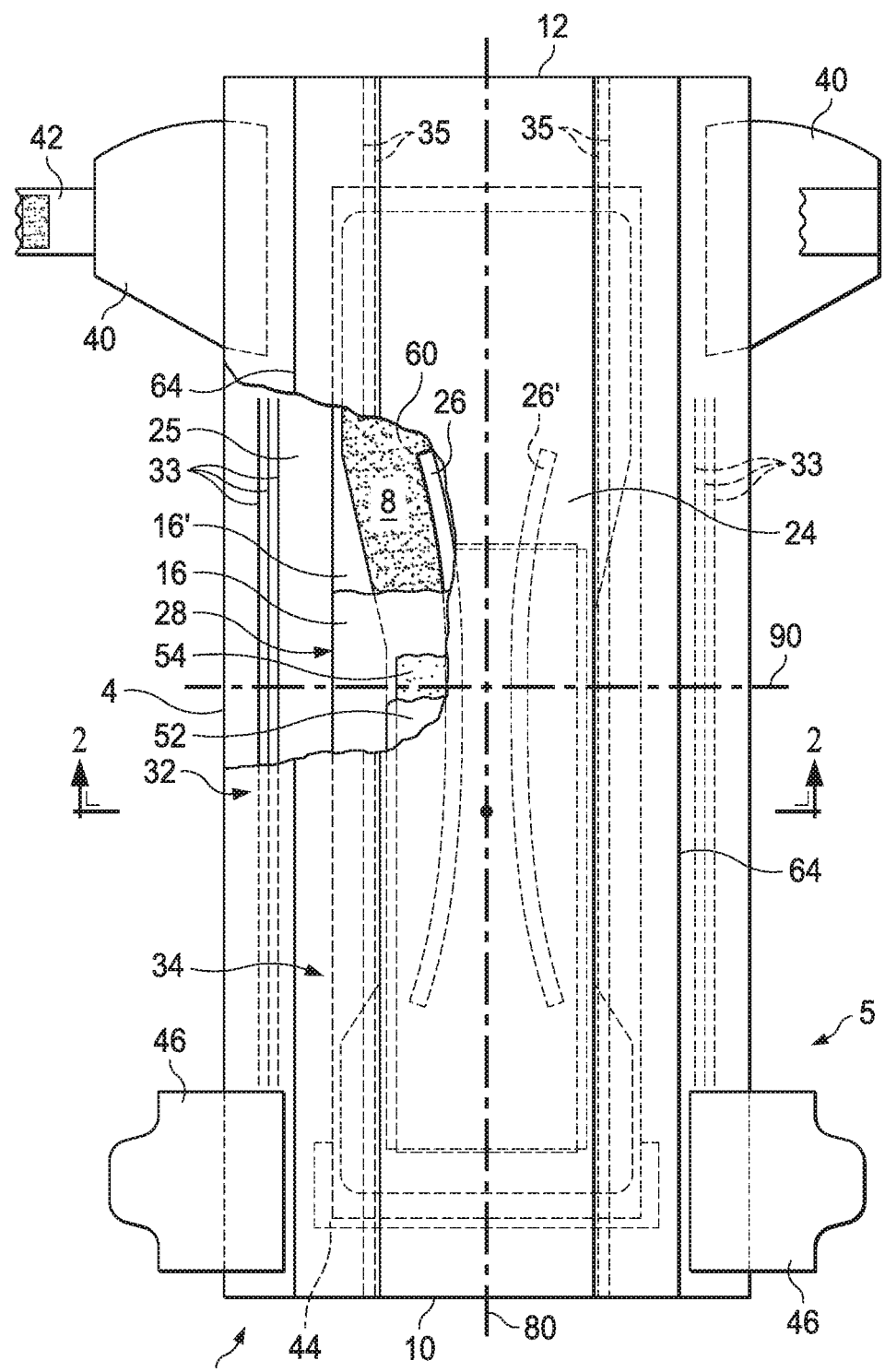
FIG. 1 is a schematic plan view of one embodiment of the present invention.

As used herein, the following terms shall have the meaning specified thereafter:

"Absorbent article" refers to articles of wear which may be in the form of pants, taped diapers, incontinent briefs and pads, feminine hygiene napkins, wound dressings, hospital garments, and the like. The "absorbent article" may be so configured to also absorb and contain various exudates such as urine, feces, and menses discharged from the body. The "absorbent article" may serve as an outer cover adaptable to be joined with a separable disposable absorbent insert for providing absorbent and containment function, such as those disclosed in PCT publication WO 2011/087503 A.

"Pant" refers to disposable absorbent articles having a pre-formed waist and leg openings. A pant may be donned by inserting a wearer's legs into the leg openings and sliding the pant into position about the wearer's lower torso. Pants are also commonly referred to as "closed diapers", "prefastened diapers", "pull-on diapers", "training pants" and "diaper-pants".

"Longitudinal" refers to a direction running substantially perpendicular from a waist edge to an opposing waist edge of the article and generally parallel to the maximum linear dimension of the article. "Transverse" refers to a direction perpendicular to the longitudinal direction.

"Inner" and "outer" refer respectively to the relative location of an element or a surface of an element or group of elements. "Inner" implies the element or surface is nearer to the wearer during wear than some other element or surface. "Outer" implies the element or surface is more remote from the wearer during wear than some other element or surface (i.e., element or surface is proximate to the wearer's garments that may be worn over the present article).

"Body-facing" and "garment-facing" refer respectively to the relative location of an element or a surface of an element or group of elements. "Body-facing" implies the element or surface is nearest to the wearer during wear than any other element or surface. "Garment-facing" implies the element or surface is most remote from the wearer during wear than any other element or surface. The garment-facing surface may face another garment of the wearer, or the atmosphere.

"Disposed" refers to an element being located in a particular place or position.

"Joined" refers to configurations whereby an element is directly secured to another element by affixing or bonding the element directly to the other element, and to configurations whereby an element is indirectly secured to another element by affixing or bonding the element to intermediate member(s) which in turn are affixed or bonded to the other element. Joining may be provided by applying adhesive agents, ultrasound, pressure, heat, or the combination thereof.

"Proximal" refers to a portion being closer or planned to be closer relative to the longitudinal center of the article, while "distal" refers to a portion being farther or planned to be farther from the longitudinal center of the article.

"Film" refers to a sheet-like material wherein the length and width of the material far exceed the thickness of the material. Typically, films have a thickness of about 0.5 mm or less.

"Water-permeable" and "water-impermeable" refer to the penetrability of materials in the context of the intended usage of disposable absorbent articles. Specifically, the term "water-permeable" refers to a layer or a layered structure having pores, openings, and/or interconnected void spaces that permit liquid water, urine, or synthetic urine to pass through its thickness in the absence of a forcing pressure. Conversely, the term "water-impermeable" refers to a layer or a layered structure through the thickness of which liquid water, urine, or synthetic urine cannot pass in the absence of a forcing pressure (aside from natural forces such as gravity). A layer or a layered structure that is water-impermeable according to this definition may be permeable to water vapor, i.e., may be "vapor-permeable".

"Hydrophilic" describes surfaces of substrates which are wettable by aqueous fluids (e.g., aqueous body fluids) deposited on these substrates. Hydrophilicity and wettability are typically defined in terms of contact angle and the strike-through time of the fluids, for example through a nonwoven fabric. This is discussed in detail in the American Chemical Society publication entitled "Contact Angle, Wettability and Adhesion", edited by Robert F. Gould (Copyright 1964). A surface of a substrate is said to be wetted by a fluid (i.e., hydrophilic) when either the contact angle between the fluid and the surface is less than 90°, or when the fluid tends to spread spontaneously across the surface of the substrate, both conditions are normally co-existing. Conversely, a substrate is considered to be "hydrophobic" if the contact angle is greater than 90° and the fluid does not spread spontaneously across the surface of the fiber.

"Extendibility" and "extensible" mean that the width or length of the component in a relaxed state can be extended or increased.

"Elasticated" and "elasticized" mean that a component comprises at least a portion made of elastic material.

"Elongation rate" means the state of elongation of a material from its relaxed, original length, namely an elongation rate of 10% means an elongation resulting in 110% of its relaxed, original length.

"Elongatable material", "extensible material", or "stretchable material" are used interchangeably and refer to a material that, upon application of a biasing force, can stretch to an elongation rate of at least 10% (i.e. can stretch to 10 percent more than its original length), without rupture or breakage, and upon release of the applied force, shows little recovery, less than about 20% of its elongation without complete rupture or breakage as measured by EDANA method 20.2-89. In the event such an elongatable material recovers at least 40% of its elongation upon release of the applied force, the elongatable material will be considered to be "elasticated" or "elastic." For example, an elastic material that has an initial length of 100 mm can extend at least to 150 mm, and upon removal of the force retracts to a length of at least 130 mm (i.e., exhibiting a 40% recovery). In the event the material recovers less than 40% of its elongation upon release of the applied force, the elongatable material will be considered to be "substantially non-elastic" or "substantially non-elastic". For example, an elongatable material that has an initial length of 100 mm can extend at least to 150 mm, and upon removal of the force retracts to a length of at least 145 mm (i.e., exhibiting a 10% recovery).

DETAILED DESCRIPTION OF THE INVENTION

General Description of the Absorbent Article

An exemplary absorbent article according to the invention in the form of a taped diaper 20 is represented in FIG. 1, which is a flattened state, with portions of the structure being cut-away to more clearly show the construction of the diaper 20. This absorbent article 20 is shown for illustration purpose only as the invention may be used for making a wide variety of absorbent articles such as pant diapers and sanitary napkins. The absorbent article may be notionally divided by a longitudinal axis 80 and a transverse axis 90.

Figure 2:
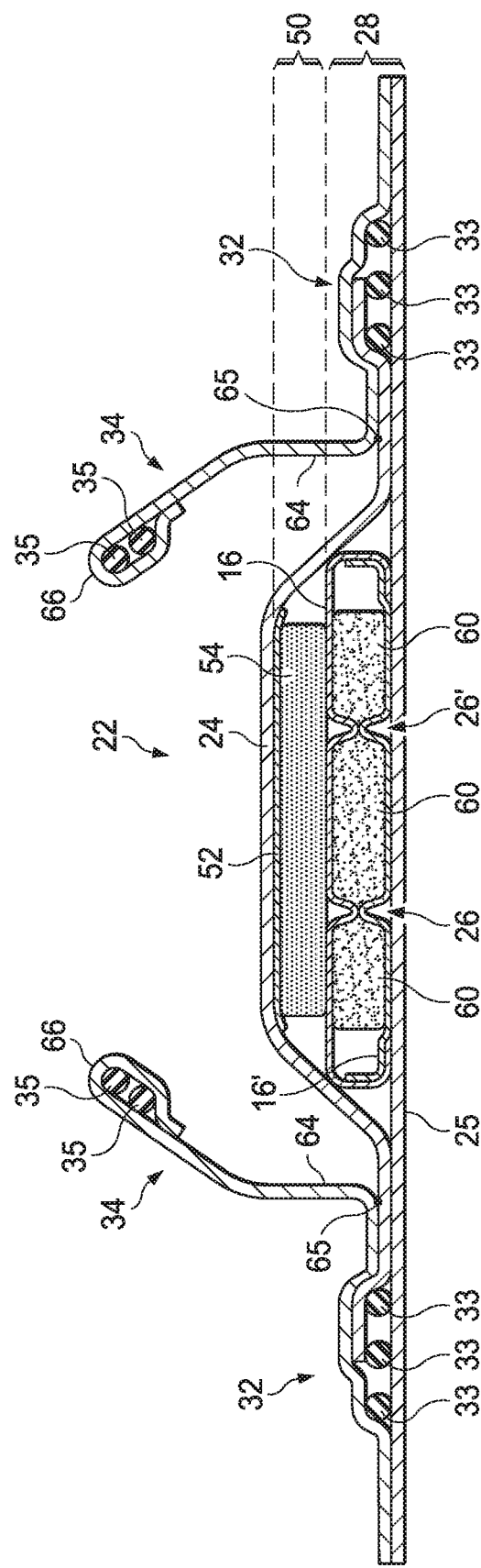
FIG. 2 is a schematic cross section view of the embodiment of FIG. 1.

FIG. 2 is a schematic cross section view of the embodiment of FIG. 1 taken along transverse axis 90. Referring to FIG. 2, the absorbent article comprises a liquid permeable topsheet 24, a liquid impermeable backsheet 25, an absorbent core 28 between the topsheet 24 and the backsheet 25, and barrier cuffs 34. The absorbent article may also comprise an acquisition-distribution system ("ADS"), which in the example represented comprises a distribution layer 54 and an acquisition layer 52, which will be further detailed in the following. The article may also comprise elasticized gasketing cuffs 32 and barrier cuffs 34 joined to the chassis of the absorbent article, typically via the topsheet and/or backsheet, and substantially planar with the chassis of the diaper.

FIG. 1 also shows typical taped diaper components such as a fastening system comprising adhesive tabs 42 attached towards the back edge of the article and cooperating with a landing zone 44 on the front of the article. While not shown, the absorbent article of the present invention may be in the form of a pad for use as a feminine sanitary napkin having a generally elongated oval shape, or an hourglass shape. The absorbent article 20 comprises a front edge 10, a back edge 12, and two side edges. The front edge 10 is the edge of the article which is intended to be placed towards the front of the user when worn, and the back edge 12 is the opposite edge.

In a taped diaper, as exemplarily shown in FIG. 1, the back edge of the diaper is typically on the side of the diaper that comprises the fastening tabs 42 and the front edge is typically on the side of the diaper that comprise the matching landing zone 44. More generally, the front of the article has typically more absorbent capacity than the back of the article. The topsheet 24, the backsheet 25, the absorbent core 28 and the other article components may be assembled in a variety of well known configurations, in particular by gluing or heat embossing. Exemplary diaper configurations are described generally in U.S. Pat. Nos. 3,860,003, 5,221,274, 5,554,145, 5,569,234, 5,580,411, and 6,004,306.

Referring to FIG. 2, the absorbent material in the absorbent core 28 may comprise at least 80% by weight of superabsorbent polymers and a core wrap enclosing the absorbent material. The core wrap may typically comprise two substrates 16 and 16' for the top side and bottom side of the core. The absorbent core 28 may further comprise at least one channel 26 and 26'.

Topsheet

The topsheet 24 is the part of the absorbent article that is directly in contact with the wearer's skin. The topsheet 24 can be joined to the backsheet 25, the core 28 and/or any other layers as is known in the art. Usually, the topsheet 24 and the backsheet 25 are joined directly to each other in some locations (e.g. on or close to the periphery of the article) and are indirectly joined together in other locations by directly joining them to one or more other elements of the article 20.

The topsheet 24 comprises a skin facing side and a core facing side. The topsheet 24 is liquid permeable, permitting liquids to readily penetrate through its thickness. The topsheet 24 is selected from material which are compliant, soft feeling, and non-irritating to the wearer's skin. A suitable topsheet may be manufactured from a wide range of materials, such as porous foams, reticulated foams, apertured plastic films, or woven or nonwoven materials of natural fibers (e.g., wood or cotton fibers), synthetic fibers or filaments (e.g., polyester or polypropylene or bicomponent polyester/polypropylene fibers or mixtures thereof), or a combination of natural and synthetic fibers. If the topsheet 24 includes nonwoven fibers, the fibers may be spunbond, carded, wet-laid, meltblown, hydroentangled, or otherwise processed as is known in the art. Suitable topsheets include spunbond polypropylene nonwoven. A suitable topsheet comprising a web of staple-length polypropylene fibers is manufactured by Veratec, Inc., a Division of International Paper Company, of Walpole, MA under the designation P-8. The topsheet 24 may have a basis weight of from about 10 gsm to about 21 gsm, or from about 12 gsm to about 18 gsm, or no more than about 15 gsm. The topsheet may have an air permeability of at least about 300 $m^3/m^2/min$ according to measurements herein. Topsheet material having relatively low basis weight and relatively high air permeability may be advantageous for quickly allowing fluid and moisture penetrate through the topsheet 24 for improving fluid handling.

Suitable formed film topsheets are also described in U.S. Pat. Nos. 3,929,135, 4,324,246, 4,342,314, 4,463,045, and 5,006,394. Other suitable topsheets may be made in accordance with U.S. Pat. Nos. 4,609,518 and 4,629,643 issued to Curro et al. Such formed films are available from The Procter & Gamble Company of Cincinnati, Ohio as "DRI-WEAVE" and from Tredegar Corporation, based in Richmond, VA, as "CLIFF-T".

Suitable natural fibers which may be comprised in the topsheet web include cellulosic plant fibers such as fibers of cotton, flax, hemp, jute, or semi-synthetic fibers derived from cellulosic material, such as rayon, visclose, or lyocell.

The skin facing side of the topsheet 24 may be treated with a hydrophilic surfactant having an HLB value of at least about 7 to improve wettability of the topsheet 24. The hydrophilic surfactant may be a nonionic surfactant. The hydrophilic surfactant may have a melting point of at least about 30° C. for ease of handling. Suitable hydrophilic surfactants may include alkylglycosides, ethoxylated sorbitan mono-, di- and tri-esters of fatty acids, ethoxylated aliphatic alcohols, silicone copolymers, and mixtures thereof. Hydrophilic surfactant may be applied in an amount of from about 0.1% to about 1% of the weight of the topsheet 24.

The skin facing side of the topsheet 24 may further be coated with a lotion comprising an emollient having plastic or fluid consistency at 20° C. and an immobilizer having a melting point of at least about 35° C. The emollient may be a material that softens, soothes, lubricates, or moisturizes the skin. The immobilizer may be a material that prevents the emollient from migrating into the interior of the absorbent article. Suitable emollients may include petrolatum, fatty acid ester, fatty alcohol ethoxylates, polysiloxanes, and mixtures thereof. Suitable immobilizers may include fatty alcohol such as cetyl alcohol and stearyl alcohol, fatty acids, polyhydroxy fatty acids, waxes, and mixtures thereof. Examples of suitable lotions include those described in U.S. Pat. Nos. 5,607,760, 5,609,587, 5,643,588, 5,968,025 and 6,716,441. The topsheet 24 may also include or be treated with antibacterial agents, some examples of which are disclosed in PCT Publication WO 95/24173. The lotion may be applied towards the transverse and longitudinal center of the topsheet for providing protection to the genital skin. The lotion may be provided in stripes extending in the longitudinal direction and spaced apart in the transverse direction. The lotion may be provided in an amount of from about 0.05 g to about 0.08 g per article.

The core facing side of the topsheet 24 may be coated with at least about 0.01 $mg/m^2$, or from about 0.05 $mg/m^2$ to about 0.2 $mg/m^2$ of calcium carbonate. It is the unexpected finding of the present invention that, by providing such calcium carbonate coating on the core facing side of the topsheet 24, this improves fluid handling, as detailed hereinbelow. This is unlike the teachings found in, for example, Japanese Patent publications H10-219568A and 2001-137285A wherein calcium carbonate is coated on the skin facing side. Providing calcium carbonate coating on the core facing side of the topsheet 24 provides benefits such as 1) avoiding interference with other coatings on the skin facing side such as hydrophilic surfactant and lotion as described above, 2) enabling having effective bondings between the topsheet and cuff material as described below, and 3) help reduce stain of fluids on the topsheet by driving the fluids towards the core.

What is meant by interference with lotion is as such. Lotion may be applied in the transverse center of the topsheet 24, for example in stripes, such that it may provide protection to the genitals and also to avoid cuff material, as lotion migrated towards the distal edge of the cuff may deteriorate the elastic members or the adhesive material for keeping the elastic members in position. Providing calcium carbonate coating on the core facing side enables such application of lotion in the transverse center of the skin facing side, while also allowing calcium carbonate applied in the transverse center of the core facing side. What is meant by reduction of perceived stain is as such. Stain is particularly noticeable for mense waste. Providing calcium carbonate coating on the core facing side drives fluids towards the core and away from the topsheet 24. By reducing the stain on the topsheet 24, this provides an appearance of clean and dry topsheet even after insult, thus provides perceived good absorbency performance.

Calcium carbonate useful herein may have a particle size of from about 10 μm to about 400 μm. Calcium carbonate may be applied in the form of particles and air sprayed, or transferred from a moving substrate. Calcium carbonate may be in the form of a suspension contained in a hot melt adhesive. Such hot melt adhesive suspension of calcium carbonate may be applied to the core facing side of the topsheet for simultaneously serving the function of joining together the topsheet 24 with the adjacent component of the absorbent article. Typically, adjacent layers and components of the absorbent article are joined together using conventional bonding methods such as adhesive coating via slot coating or spraying on the whole or part of the surface of the layer. Bonding methods may also include thermo-bonding, or pressure bonding or combinations thereof. Such bonding is not represented in the Figures (except for the bonding between the raised element of the leg cuffs 65 with the topsheet 24) for clarity and readability, but bonding between the layers of the article should be considered to be present. Among such bonding methods, hot melt adhesives may be used to improve the adhesion of the different layers, for example between the topsheet 24 and the adjacent component. The adhesive for attaching the topsheet 24 to the adjacent component may be any standard hot melt adhesive known in the art, and may be provided in stripes, spirals, or other patterns. The hot melt adhesive suspension of calcium carbonate may be coated in stripes or spirals continuous in the longitudinal direction of the article and spaced apart in the transverse direction of the article. The hot melt adhesive suspension of calcium carbonate may be coated in a repeating pattern that signals fast/effective absorbency to the user, or one that is aesthetically pleasing. The hot melt adhesive suspension of calcium carbonate may be colored such that it is visible through the topsheet.

Backsheet

The backsheet 25 is generally that portion of the article 20 positioned adjacent the garment-facing surface of the absorbent core 28 and which prevents the exudates absorbed and contained therein from soiling articles such as bedsheets and undergarments. The backsheet 25 is liquid impermeable. The backsheet 25 may be, or comprise, a thin plastic film such as a thermoplastic film having a thickness of about 0.012 mm to about 0.051 mm. Exemplary backsheet films include those manufactured by Tredegar Corporation, based in Richmond, VA, and sold under the trade name CPC2 film. Other suitable backsheet materials may include breathable materials which permit vapors to escape from the diaper 20 while still preventing exudates from passing through the backsheet 25. Exemplary breathable materials may include materials such as woven webs, nonwoven webs, composite materials such as film-coated nonwoven webs, microporous films such as manufactured by Mitsui Toatsu Co., of Japan under the designation ESPOIR NO and by Tredegar Corporation of Richmond, VA, and sold under the designation EXAIRE, and monolithic films such as manufactured by Clopay Corporation, Cincinnati, OH under the name HYTREL blend P18-3097. Some breathable composite materials are described in greater detail in PCT Application No. WO 95/16746 published on Jun. 22, 1995 in the name of E. I. DuPont; U.S. Pat. No. 5,938,648 to LaVon et al., U.S. Pat. No. 4,681,793 to Linman et al., U.S. Pat. No. 5,865,823 to Curro; and U.S. Pat. No. 5,571,096 to Dobrin et al, U.S. Pat. No. 6,946,585B2 to London Brown.

Absorbent Core

As used herein, the term "absorbent core" refers to the individual component of the article having the most absorbent capacity and comprising an absorbent material and an optional core wrap enclosing the absorbent material. The term "absorbent core" does not include the acquisition-distribution system or layer or any other component of the article which is not either integral part of the core wrap or placed within the core wrap. The absorbent core 28 may comprise absorbent material with a high amount of super-absorbent polymers (herein abbreviated as "SAP") enclosed within a core wrap. The SAP content represents at least 80% by weight of the absorbent material contained in the core wrap. The core wrap is not considered as absorbent material for the purpose of assessing the percentage of SAP in the absorbent core.

By "absorbent material" it is meant a material which has some absorbency property or liquid retaining properties, such as SAP, cellulosic fibers as well as synthetic fibers. Typically, glues used in making absorbent cores have no absorbency properties and are not considered as absorbent material. The SAP content may be higher than 80%, for example at least 85%, at least 90%, at least 95% and even up to and including 100% of the weight of the absorbent material contained within the core wrap. This provides a relatively thin core compared to conventional core typically comprising between 40-60% SAP and high content of cellulose fibers. The caliper at the point where the longitudinal axis 80 and transverse axis 90 cross may be from about 4 mm to about 12 mm, or from about 6 mm to about 10 mm.

The absorbent material may be a continuous layer present within the core wrap. In other embodiments, the absorbent material may be comprised of individual pockets or stripes of absorbent material enclosed within the core wrap. In the first case, the absorbent material may be for example obtained by the application of a single continuous layer of absorbent material. The continuous layer of absorbent material, in particular of SAP, may also be obtained by combining two absorbent layers having discontinuous absorbent material application pattern wherein the resulting layer is substantially continuously distributed across the absorbent particulate polymer material area, as taught in US 2008/0312622 A1 (Hundorf) for example. The absorbent core 28 may for example comprise a first absorbent layer and a second absorbent layer, the first absorbent layer comprising a first substrate 16 and a first layer of absorbent material, which may be 100% SAP, and the second absorbent layer comprising a second substrate 16' and a second layer of absorbent material, which may also be 100% SAP, and a fibrous thermoplastic adhesive material at least partially bonding each layer of absorbent material to its respective substrate. The stripes or land areas may be separated by junction areas. The stripes may advantageously comprise different amount of absorbent material (SAP) to provide a profiled basis weight along the longitudinal axis of the core 80'. The first substrate 16 and the second substrate 16' may form the core wrap.

SAP as used herein refer to absorbent material which are cross-linked polymeric materials that can absorb at least 10 times their weight of an aqueous 0.9% saline solution as measured using the Centrifuge Retention Capacity (CRC) test (EDANA method WSP 241.2-05E). The SAP used may in particular have a CRC value of more than 20 g/g, or more than 24 g/g, or of from 20 to 50 g/g, or from 20 to 40 g/g, or 24 to 30 g/g. The SAP useful in the present invention include a variety of water-insoluble, but water-swellable polymers capable of absorbing large quantities of fluids. Typically, SAP are spherical-like particles. In contrast to fibers, "spherical-like particles" have a longest and a smallest dimension with a particulate ratio of longest to smallest particle dimension in the range of 1-5. The SAP may have a particle sizes in the range from 45 µm to 4000 µm, more specifically a particle size distribution within the range of from 45 µm to about 2000 µm, or from about 100 µm to about 1000, 850 or 600 µm. The particle size distribution of a material in particulate form can be determined as it is known in the art, for example by means of dry sieve analysis (EDANA 420.02 "Particle Size distribution).

The type, amount, and distribution of SAP to be used in an absorbent core are adjusted according to the bodily fluids to be contained, and the autonomy of the wearer. For example, the type of SAP used for low viscosity fluids such as urine compared to those for high viscosity fluids such as menses may vary. A blend of SAPs may also be used. The fluid permeability of a superabsorbent polymer can be quantified using its Urine Permeability Measurement (UPM) value, as measured in the test disclosed European patent application number EP 12174117.7. The UPM of the SAP may for example be of at least $10 \times 10^{-7}$ cm$^3$.sec/g, or at least $30 \times 10^{-7}$ cm$^3$.sec/g, or at least $50 \times 10^{-7}$ cm$^3$.sec/g, or more, e.g. at least 80 or $100 \times 10^{-7}$ cm$^3$.sec/g. The flow characteristics can also be adjusted by varying the quantity and distribution of the SAP used in the second absorbent layer.

The core wrap may be made of a single substrate folded around the absorbent material, or may advantageously comprise two (or more) substrates which are attached to another. Typical attachments are the so-called C-wrap and/or sandwich wrap. In a C-wrap, as exemplarily shown in FIG. 2, the longitudinal and/or transversal edges of one of the substrate are folded over the other substrate to form flaps. These flaps are then bonded to the external surface of the other substrate, typically by gluing.

The core wrap may be formed by any materials suitable for receiving and containing the absorbent material. Typical substrate materials used in the production of conventional cores may be used, in particular paper, tissues, films, wovens or nonwovens, or laminate of any of these. The core wrap may in particular be formed by a nonwoven web, such as a carded nonwoven, spunbond nonwoven ("S") or meltblown nonwoven ("M"), and laminates of any of these. For example spunmelt polypropylene nonwovens are suitable, in particular those having a laminate web SMS, or SMMS, or SSMMS, structure, and having a basis weight range of about 5 gsm to 15 gsm. Suitable materials are for example disclosed in U.S. Pat. No. 7,744,576, US 2011/0268932 A1, US 2011/0319848 A1 or US 2011/0250413 A1. Nonwoven materials provided from synthetic fibers may be used, such as PE, PET and in particular PP.

If the core wrap comprises a first substrate 16 and a second substrate 16' these may be made of the same type of material, or may be made of different materials or one of the substrate may be treated differently than the other to provide it with different properties. As the polymers used for nonwoven production are inherently hydrophobic, they are preferably coated with hydrophilic coatings if placed on the fluid receiving side of the absorbent core. It is advantageous that the top side of the core wrap, i.e. the side placed closer to the wearer in the absorbent article, be more hydrophilic than the bottom side of the core wrap. A possible way to produce nonwovens with durably hydrophilic coatings is via applying a hydrophilic monomer and a radical polymerization initiator onto the nonwoven, and conducting a polymerization activated via UV light resulting in monomer chemically bound to the surface of the nonwoven. An alternative possible way to produce nonwovens with durably hydrophilic coatings is to coat the nonwoven with hydrophilic nanoparticles, e.g. as described in WO 02/064877.

Channels

The absorbent core may comprise at least one channel 26, which is at least partially oriented in the longitudinal direction of the article 80. If the following the plural form "channels" will be used to mean "at least one channel". The channels may be formed in various ways. For example the channels may be formed by zones within the absorbent material deposition area which may be substantially free of absorbent material, in particular SAP. In addition or alternatively, the channel(s) may also be formed by continuously or discontinuously bonding the top side of the core wrap to the bottom side of the core wrap through the absorbent material deposition area. The channels may be advantageously continuous but it is not excluded that the channels are intermittent. The acquisition-distribution system or any sub-layer between topsheet and absorbent core layer, or another layer of the article, may also comprise channels, which may or not correspond to the channels of the absorbent core.

Furthermore, in order to reduce the risk of fluid leakages, the longitudinal main channels typically do not extend up to any of the edges of the absorbent material deposition area, and are therefore fully encompassed within the absorbent material deposition area of the core. Typically, the smallest distance between a channel and the closest edge of the absorbent material deposition area is at least 5 mm.

Barrier Cuffs

The absorbent article may comprise a pair of barrier cuffs 34. The barrier cuffs 34 can be formed from a piece of material, typically a nonwoven, which is partially bonded to the topsheet so that a portion of the material, the barrier cuffs 34, can be partially raised away and stand up from the plane defined by the topsheet when the article is pulled flat as shown e.g. in FIG. 1. The barrier cuffs can provide improved containment of liquids and other body exudates approximately at the junction of the torso and legs of the wearer. The barrier cuffs 34 may extend at least partially between the front edge and the back edge of the article on opposite sides of the longitudinal axis. The barrier cuffs 34 are delimited by a proximal edge 64 joined to the topsheet and a free terminal edge 66, which is intended to contact and form a seal with the wearer's skin. The barrier cuffs may be joined at the proximal edge 64 with the topsheet by an anchor point 65 which may be made by adhesive, heat, pressure, or combination thereof. Whatever the joining method of the barrier cuffs 34 to the topsheet, it is preferred that materials such as lotion and calcium carbonate do not exist at the anchor point 65 to enable effective bonding of the barrier cuffs 34 to the topsheet 24.

The barrier cuffs 34 can be integral with the topsheet or the backsheet, or more typically be formed from a separate material joined to the rest of the article. Typically the material of the barrier cuffs 34 may extend through the whole length of the article but is "tack bonded" to the topsheet towards the front edge and back edge of the article so that in these sections the barrier cuff material remains flush with the topsheet. Each barrier cuff 34 may comprise one, two or more elastic strings 35 close to this free terminal edge 66 to provide a better seal.

In addition to the barrier cuffs 34, the article may comprise gasketing cuffs 32, which are joined to the chassis of absorbent article, in particular the topsheet and/or the backsheet and are placed transversely outwardly relative to the barrier cuffs 34. The gasketing cuffs 32 can provide a better seal around the thighs of the wearer. Usually each gasketing leg cuff will comprise one or more elastic string or elastic element comprised in the chassis of the diaper for example between the topsheet and backsheet in the area of the leg openings.

U.S. Pat. No. 3,860,003 describes a disposable diaper which provides a contractible leg opening having a side flap and one or more elastic members to provide an elasticized leg cuff (a gasketing cuff). U.S. Pat. Nos. 4,808,178 and 4,909,803 issued to Aziz et al. describe disposable diapers having "stand-up" elasticized flaps (barrier cuffs) which improve the containment of the leg regions. U.S. Pat. Nos. 4,695,278 and 4,795,454 issued to Lawson and to Dragoo respectively, describe disposable diapers having dual cuffs, including gasketing cuffs and barrier cuffs.

Acquisition-Distribution System

The absorbent articles of the invention may comprise an acquisition-distribution layer or system 50 (herein "ADS"). The function of the ADS is to quickly acquire the fluid and distribute it to the absorbent core in an efficient manner. The ADS may comprise one, two or more layers, which may form a unitary layer or remain discrete layers which may be attached to each other. In the examples below, the ADS comprises two layers: a distribution layer 54 and an acquisition layer 52 disposed between the absorbent core and the topsheet, but the invention is not restricted to this example.

Typically, the ADS will not comprise SAP as this may slow the acquisition and distribution of the fluid. The prior art discloses many type of acquisition-distribution systems, see for example WO 2000/59430 (Daley), WO 95/10996 (Richards), U.S. Pat. No. 5,700,254 (McDowall), WO 02/067809 (Graef). The ADS may comprise, although not necessarily, two layers: a distribution layer and an acquisition layer, which will now be exemplified in more details. The layer of the ADS positioned directly beneath the topsheet may be referred to as the secondary topsheet.

The ADS may comprise an acquisition layer 52. The acquisition layer may be disposed on the core facing side of the topsheet 24. The acquisition layer 52 may typically be or comprise a non-woven material, for example a SMS or SMMS material, comprising a spunbonded, a meltblown and a further spunbonded layer or alternatively a carded chemical-bonded nonwoven, or a spunlace nonwoven. The non-woven material may in particular be latex bonded with, such as a styrene-butadiene latex binder. Exemplary upper acquisition layers 52 are disclosed in U.S. Pat. No. 7,786, 341. Carded, resin-bonded nonwovens may be used, in particular where the fibers used are solid, round, or round hollow PET staple fibers (50/50 or 40/60 mix of 6 denier and 9 denier fibers). An exemplary binder is a butadiene/styrene latex. Further useful non-wovens are described in U.S. Pat. No. 6,645,569 to Cramer et al., U.S. Pat. No. 6,863,933 to Cramer et al., U.S. Pat. No. 7,112,621 to Rohrbaugh et al., and co patent applications US 2003/148684 to Cramer et al. and US 2005/008839 to Cramer et al.

If an acquisition layer 52 is present, it may be advantageous that this acquisition layer is larger than or least as large as the distribution layer 54 in the longitudinal and/or transversal dimension. In this way the distribution layer 52 can be deposited on the acquisition layer 54 during the manufacturing process before assembling these layers in the finished article. This simplifies handling, in particular if the acquisition layer is a nonwoven which can be unrolled from a roll of stock material. The distribution layer may also be deposited directly on the absorbent core's upper side of the core wrap or another layer of the article. Also, an acquisition layer 52 larger than the distribution layer allows to directly glue the acquisition layer to the storage core (at the larger areas). This can give increased integrity to the article and better liquid communication.

The distribution layer may be disposed between the acquisition layer and the core, and may comprise at least 50% by weight of cross-linked cellulose fibers. The cross-linked cellulosic fibers may be crimped, twisted, or curled, or a combination thereof including crimped, twisted, and curled. This type of material has been used in the past in disposable diapers as part of an acquisition system, for example US 2008/0312622 A1 (Hundorf). The cross-linked cellulosic fibers provide higher resilience and therefore higher resistance to the first absorbent layer against the compression in the product packaging or in use conditions, e.g. under baby weight. This provides the core with a higher void volume, permeability and liquid absorption, and hence reduced leakage and improved dryness. Exemplary chemically cross-linked cellulosic fibers suitable for a distribution layer are disclosed in U.S. Pat. Nos. 5,549,791, 5,137,537, WO 9534329 or US 2007/118087. Exemplary cross-linking agents include polycarboxylic acids such as citric acid and/or polyacrylic acids such as acrylic acid and maleic acid copolymers. For example, the crosslinked cellulosic fibers may have between about 0.5 mole % and about 10.0 mole % of a C2-C9 polycarboxylic acid cross-linking agent, calculated on a cellulose anhydroglucose molar basis, reacted with said fibers in an intrafiber ester crosslink bond form.

The distribution layer comprising cross-linked cellulose fibers of the invention may comprise other fibers, but this layer may advantageously comprise at least 50%, or 60%, or 70%, or 80%, or 90% or even up to 100%, by weight of the layer, of cross-linked cellulose fibers (including the cross-linking agents). Examples of such mixed layer of cross-linked cellulose fibers may comprise about 70% by weight of chemically cross-linked cellulose fibers, about 10% by weight polyester (PET) fibers, and about 20% by weight untreated pulp fibers. In another example, the layer of cross-linked cellulose fibers may comprise about 70% by weight chemically cross-linked cellulose fibers, about 20% by weight lyocell fibers, and about 10% by weight PET fibers. In another example, the layer may comprise about 68% by weight chemically cross-linked cellulose fibers, about 16% by weight untreated pulp fibers, and about 16% by weight PET fibers. In another example, the layer of cross-linked cellulose fibers may comprise from about 90-100% by weight chemically cross-linked cellulose fibers.

The distribution layer may typically have an average basis weight of from 30 to 400 g/m$^2$, in particular from 100 to 300 g/m$^2$. The density of the distribution layer may vary depending on the compression of the article, but may be of between 0.03 to 0.15 g/cm$^3$, in particular 0.08 to 0.10 g/cm$^3$ measured at 0.30 psi (2.07 kPa).

Fastening System

The absorbent article may include a fastening system. The fastening system can be used to provide transverse tensions about the circumference of the absorbent article to hold the absorbent article on the wearer as is typical for taped diapers, or to fasten the article to the undergarment by adhesive means. The fastening system may be provided as a side seam for a pant article which is already bonded. The fastening system usually comprises a fastener such as tape tabs, hook and loop fastening components, interlocking fasteners such as tabs & slots, buckles, buttons, snaps, and/or hermaphroditic fastening components, although any other known fastening means are generally acceptable. A landing zone is normally provided on the front waist region for the fastener to be releasably attached. Some exemplary surface fastening systems are disclosed in U.S. Pat. Nos. 3,848,594, 4,662,875, 4,846,815, 4,894,060, 4,946,527, 5,151,092 and 5,221,274 issued to Buell. An exemplary interlocking fastening system is disclosed in U.S. Pat. No. 6,432,098. The fastening system may also provide a means for holding the article in a disposal configuration as disclosed in U.S. Pat. No. 4,963,140 issued to Robertson et al. The absorbent article may comprise front ears 46 and back ears 40 as is known in the art. The ears can be integral part of the chassis, for example formed from the topsheet and/or backsheet as side panel. Alternatively, as represented on FIG. 1, they may be separate elements attached by gluing and/or heat embossing or pressure bonding. The back ears 40 are advantageously stretchable to facilitate the attachment of the tabs 42 on the landing zone 40 and maintain the taped diapers in place around the wearer's waist. The back ears 40 may also be elastic or extensible to provide a more comfortable and contouring fit by initially conformably fitting the absorbent article to the wearer and sustaining this fit throughout the time of wear well past when absorbent article has been loaded with exudates since the elasticized ears allow the sides of the absorbent article to expand and contract.

The absorbent article may also comprise at least one elastic waist feature (not represented) that helps to provide improved fit and containment. The elastic waist feature is generally intended to elastically expand and contract to dynamically fit the wearer's waist. The elastic waist feature preferably extends at least longitudinally outwardly from at least one waist edge of the absorbent core 28 and generally forms at least a portion of the end edge of the absorbent article. Disposable diapers can be constructed so as to have two elastic waist features, one positioned in the front waist region and one positioned in the back waist region. The elastic waist feature may be constructed in a number of different configurations including those described in U.S. Pat. Nos. 4,515,595, 4,710,189, 5,151,092 and 5,221,274.

The absorbent article may be a feminine pad comprising a fastening system which is a fastening adhesive placed on the garment-facing side of the article, which fastening adhesive secures the pad to the wearer's undergarment or panty (not represented). A portion or all of the garment-facing surface of the article may coated with fastening adhesive. Fastening adhesives suitable for this purpose may be pressure-sensitive adhesive such as those described in U.S. Pat. No. 4,917,697. The fastening adhesive is typically covered with a removable release liner in order to keep the adhesive from prematurely drying out. The release liner may form an integral wrapper for packing an individual article.

1. Sample Preparation

Samples are prepared from topsheet raw materials with hydrophilic surfactant already applied (hereinafter "raw material"). A 10 cm by 10 cm square of the raw material is cut out and weighed to the unit of 1 mg. The 10 cm by 10 cm square raw material is then applied calcium carbonate by applying chalk made of 100% calcium carbonate (such as tradename DX351 available from Umajirushi Co., Ltd., Aichi, Japan or equivalent) by hand, on the side planned to face the core, to its target coating amount. Care is taken to apply calcium carbonate as evenly as possible. The side on which the calcium carbonate is applied is the "treated surface". The Comparative Example samples are not treated with calcium carbonate. For the Comparative Example samples, the side planned to face the core is the "treated surface". The samples obtained as such are pre-conditioned at 23° C.±2° C. and 50%±2% relative humidity for two hours prior to testing below.

2. Acquisition Speed

Figure 3A:
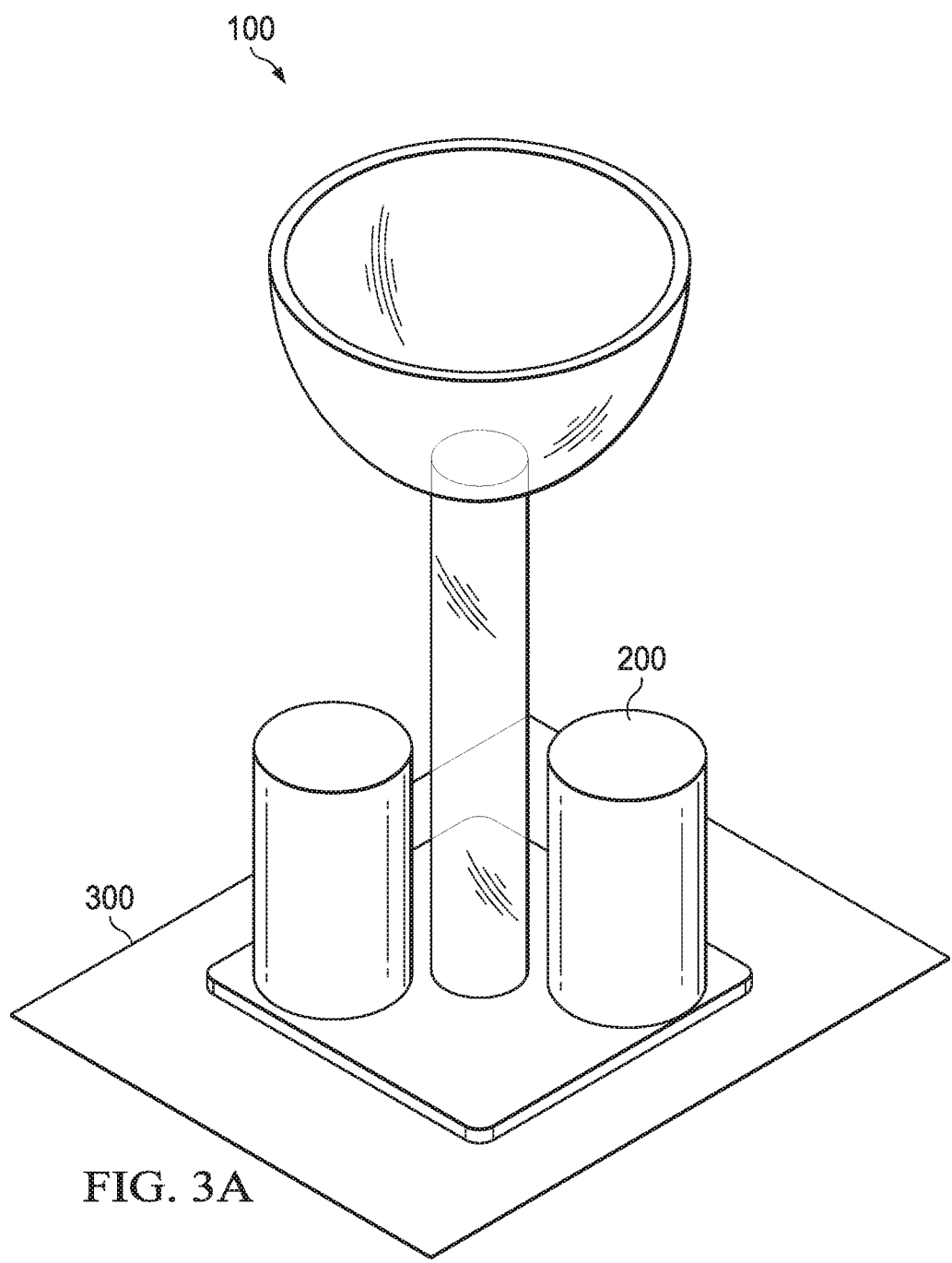
FIG. 3A is a schematic perspective view of the acquisition mess cylinder used in the measurement methods herein.
Figure 3B:
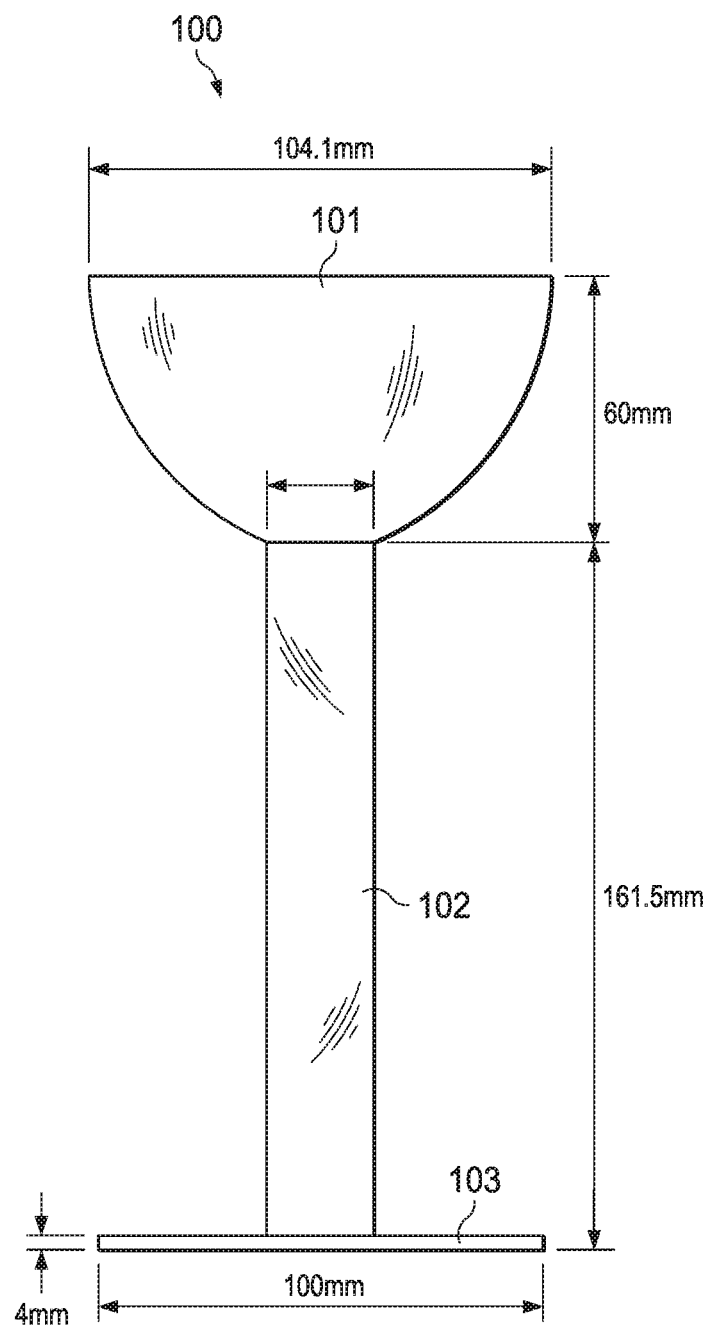
FIG. 3B is a schematic plan view of the acquisition mess cylinder.

The sample is placed, with the treated surface facing down, on an appropriate number of layers of 100% pulp paper (such as tradename 251050 available from Toyo Paper Mfg. Co., Ltd., Ehime, Japan or equivalent). The pulp paper is for absorbing overflown fluid. On the sample is placed an acquisition mess cylinder 100, as in FIGS. 3A-3B. The acquisition mess cylinder 100 comprises a funnel portion 101, a pipe portion 102, and a foot portion 103. The pipe portion 102 is opened towards the funnel portion 101 as well as the foot portion 103. The dimensions of the acquisition mess cylinder 100 are provided in FIG. 3B. Referring back to FIG. 3A, the foot portion 103 having a planar dimension similar to the sample is placed in a position that covers the sample as completely as possible. A number of weights 200 may be provided on the foot portion 103 to keep it from moving during measurement. The weights 200 should not touch the sample or the underlying paper. Predetermined amounts of artificial urine (10 ml, 25 ml, 50 ml, 75 ml, respectively) are delivered from a beaker to the acquisition mess cylinder 100. The time from which the predetermined amount is completely delivered to the acquisition mess cylinder; to the time at which the predetermined amount is completely drained from the acquisition mess cylinder 100 is measured. The same test is run 3 times and the average time up to 0.01 seconds is recorded. For the Acquisition Speed test, the shorter (lower value of) the time, the better the fluid handling property of the sample.

3. Re-Wet

The sample is placed on the opening side of an 100 ml open cylindrical beaker, such that the center of the sample is approximately matching the center of the opening of the beaker, with the treated surface facing down. The portion of the sample matching the opening of the beaker facing the atmosphere is called the "test surface". The portions of the sample draping on the vertical walls of the beaker are fixed on the beaker with adhesive tape with care not to provide additional tension on the test surface. Tape should not cover any portion of the test surface. In this test, 2 ml of artificial urine is placed on the same test surface for consecutive 3 times, representing 3 gushes of urine assulting the sample.

An amount of 2 ml (first gush) of artificial urine is placed on the test surface of the sample using a spoit and within a period of 10-12 seconds. A time of 60 seconds is measured from the instant the 2 ml articifial urine is completely placed on the test surface. After 60 seconds, the amount of artificial urine remaining on the test surface is absorbed by a pre-weighed tissue (the tissue is for providing an inert medium to remove the artificial urine) and the weight of remaining artificial urine is recorded to 0.01 g. Immediately after the remaining artifical urine of the first gush is removed from the test surface, another 2 ml (second gush) of artificial urine is placed on the test surface in the same manner, 60 seconds is measured, and after 60 seconds the amount of artificial urine remaining on the test surface is absorbed by a tissue and weighed. Immediately after the remaining artifical urine of the second gush is removed from the test surface, another 2 ml (third gush) of artificial urine is placed on the test surface in the same manner, 60 seconds is measured, and after 60 seconds the amount of artificial urine remaining on the test surface is absorbed by a tissue and weighed.

The same test is run for 5 times and the remaining artificial urine weights per gush are averaged to 0.01 g. For the Re-wet test, the lighter (lower value of) the weight, the better the fluid handling property of the sample.

4. Air Permeability Test

Air permeability is tested using a TexTest FX3300 Air Permeability Tester (available from Advanced Testing Instruments, Greer, SC) with a custom made 1 cm² circular aperture (also available from Advanced Testing Instruments) or equivalent instrument. The instrument is calibrated according to the manufacturer's procedures. Only the Comparative Example sample is tested.

For this test, the sample is further cut out in a dimension of an approximately 3 cm by 3 cm square. The sample is centered over the measurement port such that it completely covers the port. The sample is gently extended in its longitudinal direction until taut so that it lies flat across the port. Adhesive tape is applied to secure the sample across the port in its extended state for testing. Tape should not cover any portion of the measurement port. The test pressure is set to allow air to pass through the sample. The pressure is set for 125 Pa. The sample ring is closed and the measuring range is adjusted until the range indicator shows green to indicate that the measurement is within the accepted limits of the instrument. The air permeability is recorded to the nearest 0.1 m³/m²/min.

EXAMPLES

Material Examples

A 12 gsm spunbond nonwoven material FTXNL SSS P10 available from Fibertex (MRMP #95905774) was treated as such and subject to the Acquisition Speed, Re-wet, and Air Permeability measurements as described above to provide results shown in Table 1.

TABLE 1

|  | Comparative Example | Example 1 | Example 2 |
| --- | --- | --- | --- |
| Calcium carbonate amount (mg/m²) | 0 | 0.05 | 0.1 |
| Calcium carbonate particle size (μm) | NA | 10-40 | 10-40 |
| Surfactant amount (%) | 0.51 | 0.51 | 0.51 |
| Air permeability (m³/m²/min) | 302 | NA | NA |
| Acquisition speed (second) 10 ml | 4.05 | 4.95 | 4.87 |
| Acquisition speed (second) 25 ml | 11.36 | 10.75 | 11.73 |
| Acquisition speed (second) 50 ml | 32.25 | 27.07 | 24.56 |
| Acquisition speed (second) 75 ml | 45.95 | 36.58 | 32.78 |
| Re-wet (g) First gush | 1.98 | 0.98 | 1.11 |
| Re-wet (g) Second gush | 2.04 | 0.48 | 2.09 |
| Re-wet (g) Third gush | 2.10 | 2.01 | 2.14 |

Examples 1-2 meeting the requirements of the present invention provide good Acquisition Speed and Re-wet properties, compared to Comparative Example having no calcium carbonate treatment.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm." Further, every numerical range given throughout this specification includes every narrower numerical range that falls within such broader numerical range.

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising;
    a topsheet having a skin facing side and a core facing side, the topsheet being liquid permeable and having the core facing side coated with at least about 0.01 mg/m², of calcium carbonate;
    a backsheet which is liquid impermeable; and
    an absorbent core comprising an absorbent material, the absorbent core disposed between the topsheet and the backsheet; and
    wherein the calcium carbonate is coated in the form of a suspension contained in a hot melt adhesive, the hot melt adhesive suspension of calcium carbonate is coated in stripes or spirals continuous in the longitudinal direction of the article and spaced apart in the transverse direction of the article.

2. The article of claim 1 wherein the calcium carbonate has a particle size of from about 10 μm to about 400 μm.

3. The article of claim 1 wherein the calcium carbonate in the form of particle is air sprayed on the topsheet.

4. The article of claim 1 wherein the calcium carbonate in the form of particle is transferred from a moving substrate to the moving topsheet.

5. The article of claim 1 wherein the topsheet is a nonwoven having a basis weight of no more than about 15 gsm.

6. The article of claim 1 wherein the topsheet has an air permeability of at least about 300 m³/m²/min according to measurements herein.

7. The article of claim 1 wherein the topsheet comprises cotton fibers.

8. The article of claim 1 wherein the absorbent core comprises at least about 80% of superabsorbent polymers.

9. The article of claim 1 wherein the article further comprises a pair of barrier cuffs along the transverse side edges.

10. The article of claim 1 wherein the skin facing side of the topsheet is coated with from about 0.1% to about 1% per weight of the topsheet of a hydrophilic surfactant.

11. The article of claim 10 wherein the skin facing side of the topsheet is further coated with from about 0.05 g to about 0.08 g per article of a lotion.

12. The article of claim 1 wherein the article is a taped diaper, a pant diaper, or a sanitary napkin.

* * * * *